United States Patent
Navale et al.

(10) Patent No.: US 10,030,089 B2
(45) Date of Patent: Jul. 24, 2018

(54) SUGAR FREE, STATISTICAL COPOLYMERS MADE FROM AT LEAST THREE MONOMERS

(71) Applicant: REGENTS OF THE UNIVERSITY OF MINNESOTA, Minneapolis, MN (US)

(72) Inventors: Tushar S. Navale, Mumbai (IN); Jeffrey M. Ting, Minneapolis, MN (US); Frank S. Bates, St. Cloud, MN (US); Theresa M. Reineke, Vadnais Heights, MN (US)

(73) Assignee: THE REGENTS OF THE UNIVERSITY OF MINNESOTA, Minneapolis, MN (US)

( * ) Notice: Subject to any disclaimer, the term of this patent is extended or adjusted under 35 U.S.C. 154(b) by 97 days.

(21) Appl. No.: 14/889,290

(22) PCT Filed: May 6, 2014

(86) PCT No.: PCT/US2014/036991
§ 371 (c)(1),
(2) Date: Nov. 5, 2015

(87) PCT Pub. No.: WO2014/182713
PCT Pub. Date: Nov. 13, 2014

(65) Prior Publication Data
US 2016/0083492 A1    Mar. 24, 2016

Related U.S. Application Data

(60) Provisional application No. 61/819,928, filed on May 6, 2013.

(51) Int. Cl.
*C08F 220/28* (2006.01)
*A61K 47/32* (2006.01)

(52) U.S. Cl.
CPC ............ *C08F 220/28* (2013.01); *A61K 47/32* (2013.01); *C08F 2220/281* (2013.01)

(58) Field of Classification Search
CPC ... C08F 220/28; C08F 2220/281; A61K 47/32
See application file for complete search history.

(56) References Cited

U.S. PATENT DOCUMENTS

2002/0156220 A1* 10/2002 Meyer .................. C08F 246/00
526/319

FOREIGN PATENT DOCUMENTS

| CN | 102875945 A | 1/2013 |
| EP | 2 551 338 A1 | 1/2013 |
| WO | 2014/099512 A2 | 6/2014 |

OTHER PUBLICATIONS

Aldrich, Handbook of Fine Chemicals and Laboratory Equipment, 2002, Milwaukee, WI, p. 1488.*
Ting et al, ACS Macro Letters, Precise Compositional Control and Systematic Preparation of Multimonomeric Statistical Copolymers, 2013, 2, pp. 770-774.*
The International Search Report (ISR) with Written Opinion for PCT/US2014/036991 dated Aug. 25, 2014, pp. 1-8.
The State Intellectual Property Office of the People's Republic of China Patent Search Report for Cn Application No. 2014800255583 dated Nov. 9, 2016, pp. 1-2.

* cited by examiner

*Primary Examiner* — Paul A Zucker
(74) *Attorney, Agent, or Firm* — McDonnell Boehnen Hulbert & Berghoff LLP (57) ABSTRACT

Disclosed herein are polymers made from at least three monomers of formulae (I), (II), (III), and (IV) that may be used in pharmaceutical formulations. These polymers comprise a hydrocarbon backbone and are made from monomers that contain at least one carbon-carbon double bond. Methods of making the polymers are also disclosed.

17 Claims, 2 Drawing Sheets

SUGAR FREE, STATISTICAL COPOLYMERS MADE FROM AT LEAST THREE MONOMERS

CROSS REFERENCE TO RELATED APPLICATIONS

This application claims priority from International Application No. PCT/US2014/036991, filed, filed May 6, 2014, which claims the benefit of U.S. Provisional Application No. 61/819,928 filed May 6, 2013. The disclosures of all these applications are herein incorporated by reference in their entirety.

BACKGROUND OF THE INVENTION

Many drugs have low water solubility, and as a result, low bioavailability. In an effort to increase the bioavailability of these drugs, various formulation techniques are used. One known method includes combining such drugs with a pharmaceutically acceptable water-soluble polymer, such as an esterified cellulose ether, in an organic solvent that is optionally blended with water, to form a solution, and then spray-drying the solution. Such dry formulations 1) reduce the crystallinity of the drug, thereby minimizing the activation energy necessary for its dissolution, 2) establish hydrophilic conditions around the drug molecules, and 3) result in the improved solubility and bioavailability of the drug, i.e., its in vivo absorption by an individual upon ingestion. One commonly used esterified cellulose ether is hydroxypropyl methylcellulose acetate succinate. Unfortunately, known polymers often are not ideally suited for increasing the solubility of poorly soluble drugs as they were historically designed for other applications such as coatings.

SUMMARY OF THE INVENTION

The invention provides novel polymers which are suitable for improving the solubility of drugs. The polymers of the disclosure can be manufactured to have desirable properties and targetable length scales of intermolecular associations. The polymers of the disclosure have also substantially predetermined multicomponent chemical compositions and molecular weights.

Thus, in one aspect, disclosed herein are polymers having an acrylate-derived backbone, where the polymer comprises monomeric units derived from at least three monomers selected from the group consisting of:

(I)

(II)

(III)

(IV)

wherein at each occurrence, $R_1$, $R_2$ and $R_3$ are independently H or methyl;

$R_4$ is H or $C_1$-$C_6$ alkyl; and $R_6$ is $C_1$-$C_6$ alkyl;

wherein the $C_2$-$C_6$ hydroxyalkyl group has one or two OH groups.

In certain aspects, the polymer is free or substantially free of monomeric units derived from compound of formula (V):

(V)

wherein each $R_{10}$ is independently H, $C_1$-$C_4$ alkyl, $C_2$-$C_4$ alkanoyl, $C_2$-$C_5$ alkenoyl, —$C_1$-$C_4$ alkyl-aryl, or -alkanoylaryl.

Another aspect discloses polymers having an acrylate-derived backbone, where the polymer consists essentially of at least three monomeric units derived from monomers selected from the group consisting of:

(I)

(II)

wherein
at each occurrence, $R_1$, $R_2$ and $R_3$ are independently H or methyl;
$R_4$ is H or $C_1$-$C_6$ alkyl; and
$R_6$ is $C_1$-$C_6$ alkyl;
wherein the $C_2$-$C_6$ hydroxyalkyl group has one or two OH groups.

In another aspect disclosed herein are pharmaceutical formulations comprising the aforementioned polymers.

In another aspect, disclosed herein are methods of making the aforementioned polymers.

DETAILED DESCRIPTION

One aspect of the disclosure provides polymers having an acrylate-derived backbone, where the polymer comprises at least three monomeric units derived from monomers that are selected from the group consisting of formula (I), (II), (III), and (IV) as described above. As one of skill would understand, the polymers of the disclosure may contain different terminal end groups depending, for example, on the initiators used and the reaction conditions.

In certain embodiments, the monomeric units that make up the polymer comprise monomers of formula (I), (II), and (III). In other embodiments, the monomeric units that make up the polymer comprise monomers of formula (I), (III), and (IV). In certain embodiments, the monomeric units that make up the polymer comprise monomers of formula (II), (III), and (IV). In other embodiments, the monomeric units that make up the polymer comprise monomers of formula (I), (II), and (IV). In certain embodiments, the monomeric units that make up the polymer comprise monomers of formula (I), (II), (III), and (IV).

In certain embodiments, the polymer as described above is comprised of at least about 50 mol % of monomeric units are derived from monomers of formula (I), (II), (III), or (IV). In other embodiments, monomeric units derived from monomers selected from those of formula (I), (II), (III), and (IV) comprise at least about 55 mol %, or at least about 60 mol %, or at least about 65 mol %, or at least about 70 mol %, or at least about 75 mol %, or at least about 80 mol %, or at least about 85 mol %, or at least about 90 mol %, or at least about 92 mol %, or at least about 95 mol %, or at least about 96 mol %, or at least about 97 mol %, or at least about 98 mol %, or at least about 99 mol % of the polymer. The remaining monomers may be selected from a variety of typical alkene monomers that undergo traditional radical polymerization, and would be apparent to those of skill in the art.

In other embodiments, the disclosure provides polymers having an acrylate-derived backbone, where the polymer consists essentially of at least three monomeric units derived from monomers that are selected from the group consisting of formula (I), (II), (III), and (IV) as described above.

In other embodiments, the disclosure provides polymers having an acrylate-derived backbone, where the polymer consists of at least three monomeric units derived from monomers that are selected from the group consisting of formula (I), (II), (III), and (IV) as described above.

In one embodiment, the polymer as described above is where at least one occurrence of $R_1$ is H; more preferably, at least two occurrences of $R_1$ are H; and still more preferably, at least three occurrences of $R_1$ are H. In one particularly preferred embodiment, all occurrences of $R_1$ are H. In another embodiment, all occurrences of $R_1$ are methyl.

In an embodiment of the above, at least one occurrence of $R_2$ is H; more preferably, at least two occurrences of $R_2$ are H; and still more preferably, at least three occurrences of $R_2$ are H. In one particularly preferred embodiment, all occurrences of $R_2$ are H. In another embodiment, all occurrences of $R_2$ are methyl.

In another embodiment of the above, at least one occurrence of $R_3$ is H; more preferably, at least two occurrences of $R_3$ are H; and still more preferably, at least three occurrences of $R_3$ are H. In one particularly preferred embodiment, all occurrences of $R_3$ are H. In another embodiment, all occurrences of $R_3$ are methyl.

In another embodiment of the above, at least one $R_4$ is H or $C_1$-$C_6$ alkyl. Preferably, at least one $R_4$ is H or $C_1$-$C_4$ alkyl. Still more preferably, at least one $R_4$ is H. In another embodiment, all occurrences of $R_4$ are H. Alternatively, at least one $R_4$ is $C_1$-$C_4$ alkyl or more preferably, $C_1$-$C_3$ alkyl, $C_1$-$C_2$ alkyl or most preferably, methyl. In a particularly preferred embodiment, one $R_4$ is methyl, while the other is H.

In another embodiment of the above, $R_6$ is $C_1$-$C_6$ alkyl. More preferably, $R_6$ is $C_1$-$C_4$ alkyl. Still more preferably, $R_6$ is $C_1$-$C_2$ alkyl. Most preferably, $R_6$ is methyl.

In one embodiment of the above-described polymer, the monomer of formula (I) has the formula:

In another embodiment of the above, in the monomer of formula (II), the ($C_2$-$C_6$ alkyl) is a straight chain or branched. More preferably, the ($C_2$-$C_6$ alkyl) group is a ($C_2$-$C_4$ alkyl) group. In a preferred embodiment, the monomer of formula (II) has the formula:

In still another embodiment of the above, in the monomer of formula (III), the ($C_2$-$C_6$ hydroxyalkyl) is straight chained or branched. More preferably, the ($C_2$-$C_6$ hydroxyalkyl) group is a ($C_2$-$C_4$ hydroxyalkyl) group. In a preferred embodiment, the monomer of formula (III) has the formula:

or combinations thereof. Still more preferably, the monomer of formula (III) has the formula:

or combinations thereof.

In yet still another embodiment of the above, in the monomer of formula (IV), the ($C_2$-$C_6$ alkyl) group is a straight chain or branched. More preferably, the ($C_2$-$C_6$ alkyl) group is a ($C_2$-$C_4$ alkyl) group. In a preferred embodiment, the monomer of formula (IV) has the formula:

or combinations thereof. Still more preferably, the monomer of formula (IV) has the formula:

or combinations thereof. In one embodiment of the above, the polymer comprises monomers of formulae (I) and (II), (I) and (III), or (I) and (IV). In another embodiment of the above, the polymer comprises monomers of formulae (II) and (III), or (II) and (IV). In still another embodiment of the above, the polymer comprises monomers of formulae (III) and (IV).

In certain embodiments, the polymers as described herein have a molecular weight within the range of from about 500 to about 500,000 g/mol. In other embodiments, the molecular weight is about 750 to about 500,000 g/mol, or about 1,000 to about 500,000, or about 10,000 to about 500,000, or about 15,000 to about 500,000, or about 20,000 to about 500,000, or about 500 to about 200,000 g/mol, or about 1,000 to about 200,000, or about 10,000 to about 200,000, or about 15,000 to about 200,000, or about 20,000 to about 200,000, or about 500 to about 100,000 g/mol, or about 1,000 to about 100,000, or about 10,000 to about 100,000, or about 15,000 to about 100,000, or about 20,000 to about 100,000, or about 1,000 to about 50,000, or about 10,000 to about 50,000, or about 15,000 to about 50,000, or about 20,000 to about 50,000, or about 10,000 to about 40,000, or about 15,000 to about 40,000, or about 20,000 to about 40,000, or less than about 500,000, or less than about 250,000, or less than about 100,000, or less than about 75,000, or less than about 70,000, or less than about 60,000, or less than about 50,000, or less than about 40,000, or less than about 30,000 g/mol. In one embodiment, the polymers as described herein have a molecular weight of about 10,000 to about 50,000 g/mol. In another embodiment, the polymers as described herein have a molecular weight of about 20,000 to about 40,000 g/mol. The person of ordinary skill in the art can, in view of the methods described herein, prepare polymers having a desired molecular weight.

The polymers produced according to this disclosure include statistical copolymers (SCPs). SCPs are long macromolecular chains consisting of two or more units whose chemical composition hinges on their constituents' relative concentrations and reactivities. SCPs typically include monomers with desirable functionalities at specific compositions to develop well-defined morphologies and physical properties. Thus, as used herein, the term "statistical polymer" or "statistical copolymer" as used herein, means a polymer that has a distribution of the monomer units along the copolymer chain that follows some statistical law, for example, Bernoullian (zero-order Markov) or first- or second-order Markov. In general, the statistical copolymers have monomeric units that have cross-reactivity ratios close to 1. Copolymers formed via Bernoullian processes have the two monomer units distributed randomly and are referred to as "random copolymers." In some embodiments, the polymers of the disclosure may be random copolymers.

It is known to those skilled in the art that monomers such as those described above can be polymerized by a variety of methods including free radical polymerization solution, emulsion polymerization, bulk polymerization, and so-called controlled radical polymerizations such as atom transfer radical polymerization, nitroxide mediated polymerization, and reversible addition-fragmentation chain transfer polymerization.

In another embodiment, the method of making the polymerized compositions comprises treating the at least three monomers, with a free radical initiator in the presence of a chain transfer agent. An example of such a method is reversible addition-fragmentation chain transfer (RAFT).

Free radical initiators are well known in the art and include azo compounds, halogens, and organic peroxides. A preferred class of initiators is the azo compounds. Examples of preferred free radical initiators include 1,1'-azobis(cyclohexanecarbonitrile) (abbreviated as ABCN); 4,4'-azobis(4-cyanopentanoic acid; and azobisisobutyronitrile (abbreviated as AIBN), with AIBN being particularly preferred.

Chain transfer agents are known in the art and include thiols, halocarbons, xanthates, dithiobenzoates, dithiocarbamates, and trithiocarbonates. Examples of chain transfer agents include bromotrichloromethane, isooctyl 3-mercaptopropionate, tert-nonyl mercaptan (mixture of isomers), pentaerythritol tetrakis(3-mercaptopropionate), 4,4'-thiobisbenzenethiol, trimethylolpropane tris(3-mercaptopropionate), Cyanomethyl methyl(phenyl)carbamodithioate, Cyanomethyl dodecyl trithiocarbonate, 2-Cyano-2-propyl benzodithioate, 4-Cyano-4-(phenylcarbonothioylthio)pentanoic acid, 2-Cyano-2-propyl dodecyl trithiocarbonate, 4-Cyano-4-[(dodecylsulfanylthiocarbonyl)sulfanyl]pentanoic acid, 2-(Dodecylthiocarbonothioylthio)-2-methylpropionic acid, and 4-cyano-4-(propylsulfanylthiocarbonyl)sulfanylpentanoic acid (CPP), which has the following formula:

One preferred chain transfer agent is CPP.

The time necessary to complete the polymerization reaction depends on the polymerization method used. Typical reaction times are from a few minutes to a week, when using RAFT.

The temperature used to complete the polymerization reaction depends on the reactants and the polymerization protocol used. Typical polymerization temperatures are from 20° C. up to the boiling point of the solvent(s)/reagents used in the reaction. Typical temperatures when using RAFT are 60-80° C., with 65-75° C. being preferred. If nitroxide mediated polymerization is used, temperatures up to 135° C. may be used.

The use of a solvent in the polymerization reactions is optional. Examples that can be used in the preparation of the claimed polymerized compositions include dimethylformamide (DMF), tetrahydrofuran (THF), toluene, xylenes, 1,4-dioxane, DMSO, methanol, ethanol, isopropanol, water, and combinations thereof.

The resulting materials may be purified using methods known in the art, such as precipitation, evaporation of volatiles to dryness, dialysis, fractionation, chromatography or trituration.

In another embodiment, disclosed herein are pharmaceutical formulations comprising the polymerized compositions described herein and at least one active pharmaceutical ingredient. Such formulations are solid dispersions that often contain hydrophobic drugs (e.g., probucol phenytoin, griseofulvin, itraconazole, ketoconazole, or danazol), wherein the formulation effectively inhibits drug crystallization in the solid-state (long-term shelf life and storage) and promotes rapid dissolution and supersaturation maintenance in the solution-state (enhanced bioavailability). While the polymerized components can be used as excipients for a vast array of drugs, the anticipated use centers on using determined relationships to optimize excipient design and formulation. This purpose can be applicable to other fields of active delivery beyond pharmaceuticals, including agriculture, coatings, food technology, personal care, and high energy materials. Other excipients, glidants, and additives may also be present in the formulations disclosed herein.

In another embodiment, disclosed herein are methods of increasing the solubility of a drug (also known as an active pharmaceutical ingredient), the methods comprising formulating the drug with the polymerized compositions disclosed herein.

Disclosed herein are racemic mixtures as well as resolved (and partially resolved) enantiomers. The resolution of enantiomers is known in the art and encompasses methods such as chiral chromatography, and fractional crystallization.

Deuterated analogs of the compounds disclosed herein are also contemplated by the instant disclosure.

Definitions

Throughout this specification, unless the context requires otherwise, the word "comprise" and "include" and variations (e.g., "comprises," "comprising," "includes," "including") will be understood to imply the inclusion of a stated component, feature, element, or step or group of components, features, elements or steps but not the exclusion of any other integer or step or group of integers or steps.

As used in the specification and the appended claims, the singular forms "a," "an" and "the" include plural referents unless the context clearly dictates otherwise.

"Alkanoyl" is a group of the formula "—C(O)-alkyl."

"Alkenyl" is a group of the formula "—C(O)-alkenyl."

"Alkanoylaryl" is a group of the formula "—C(O)-alkyl-aryl."

The term "alkyl" as used herein, means a straight chain or branched hydrocarbon containing from 1 to 20 carbon atoms unless otherwise specified. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl. In some instances, the number of carbon atoms in the alkyl group is identified, e.g., $C_1$-$C_6$ alkyl. In such cases, the alkyl group has one to six carbons.

The term "alkenyl" as used herein, means a straight chain or branched hydrocarbon containing from 1 to 20 carbon atoms and also containing at least one carbon-carbon double bond, and up to two carbon-carbon double bonds. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, 3-decenyl, and 3,7-dimethylocta-2,6-dienyl.

The term "aryl" as used herein, means a phenyl (i.e., monocyclic aryl), or a bicyclic ring system containing at least one phenyl ring or an aromatic bicyclic ring in the aromatic bicyclic ring system, or a polycyclic ring system containing at least one phenyl ring. The rings may be fused, such as in a naphthyl group, or they may be pendant, as in biphenyl. The bicyclic aryl can be azulenyl, naphthyl, or a phenyl fused to a cycloalkyl, a cycloalkenyl, or a heterocyclyl. The bicyclic or polycyclic aryl is attached to the parent molecular moiety through any carbon atom contained within the phenyl portion of the bicyclic or polycyclic system, or any carbon atom with the napthyl, azulenyl, anthracene, or pyrene ring. More preferably, the aryl groups consist of no more than two aromatic rings. Examples of preferred aryl groups include phenyl, naphthyl, biphenyl, indene and anthracene. More preferred are phenyl and naphthyl. The most preferred aryl group is phenyl.

"Hydroxyalkyl" is an alkyl group substituted with at least one and up to three OH groups. More preferably, the hydroxyalkyl group is substituted with no more than two OH groups.

EXAMPLES

The polymers of the disclosure are illustrated further by the following examples, which are not to be construed as limiting the disclosure in scope or spirit to the specific procedures and compounds described in them.

Example 1: General RAFT Methodology

In an effort to at least partially control the RAFT polymerization process, the relative reactivities at 70° C. (in DMF) between monomer pairs were measured to predict the feed ratio necessary for synthesizing well-defined compositions via the Walling-Briggs model. Furthermore, incorporation of the Skeist model addressed possible compositional drift, providing a simple paradigm for exerting control over macromolecular chemical architecture in a stochastic process.

The polymer length and chemical composition are tunable to simultaneously control key excipient parameters, such as hydrophobicity, hydrogen bonding, ionizability, pH response, thermal response, and degradability.

Seven free radical polymerization runs were carried out for methyl acrylate (MA) and 2-acetoxypropyl acrylate (also referred to as 2-propylacetyl acetate acrylate or PAA), with the feed monomer mole fraction ranging from 0.10 to 0.90. The AIBN concentration was kept at 1000 time less than the total monomer concentration. For instance, in run 6 the following was charged to a dried NMR tube: MA (250 μL of 3 M solution in DMF-d$^7$, 0.75 mmol), PAA (83 μL of 3 M solution in DMF-d$^7$, 0.25 mmol), and AIBN (10 μL of 0.1 M solution in DMF-d$^7$, 0.001 mmol). After closing the NMR tube with rubber septum, dry nitrogen was bubbled for 15 minutes to remove dissolved oxygen. The NMR tube was then capped with a polypropylene cap and sealed with high-temperature tape under elevated nitrogen flow.

The sample was analyzed by $^1$H NMR in a Varian Inova 300 spectrometer at 22° C. to determine the initial monomer feed. The polymerization was then conducted by raising the temperature to 70° C. with the total monomer conversion kept below 15%. The total monomer conversion and molar ratio of MA to PAA in the polymer was calculated by comparing the integration of the three methoxy protons (—OCH$_3$) in MA (3.77 ppm) to corresponding methoxy protons in the copolymer (3.72 ppm), as well as the integration of the acetyl proton (—COCH$_3$) in PAA (2.01-2.06 ppm) to corresponding acetyl protons in the copolymer (2.07-2.12 ppm). A nonlinear fit $F_1=(r_{12}f_1^2+f_1f_2)/((r_{12}f_1^2+2f_1f_2+r_{21}f_2^2)$ was applied to the composition data to determine the resultant reactivity ratios $r_{MA-PAA}$=0.30, $r_{PAA-MA}$=0.81.

Example 2: Synthesis of 2-Propylacetyl Acrylate (PAA) by Acetylation of 2-Hydroxypropyl Acrylate (HPA)

Figure 1:
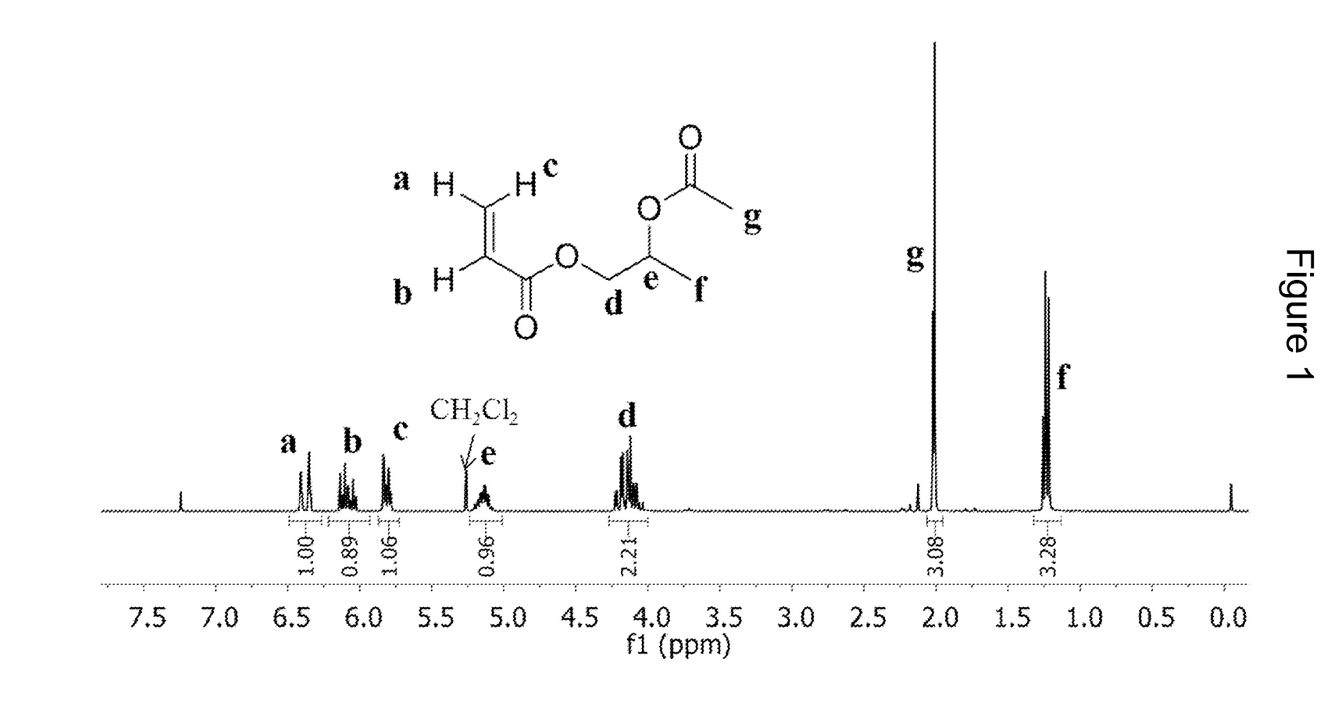
FIG. 1 shows $^1$H NMR spectra of acetoxypropyl acrylate.

4-Dimethylaminopyridine (12.22 g, 100 mmol) and acetyl chloride (7.85 g, 100 mmol) were added to a well-mixed solution of 2-hydroxypropyl acrylate (HPA) (13.01 g, 100 mmol) in 200 mL of dichloromethane. The solution was stirred overnight at room temperature. The reaction mixture was diluted with about 300 mL water. The organic layer was separated, washed twice with 150 mL 5% hydrochloric acid (HCl) and 200 mL brine, dried with anhydrous MgSO$_4$, and evaporated under vacuum to afford 2-propylacetyl acrylate as a clear colorless liquid (16.5 g, 96% yield). $^1$H NMR (CDCl$_3$): δ 1.26 (m, 3H, —CH—CH$_3$); 2.04 (s, 3H, CO—CH$_3$); 4.02-4.26 (m, 2H, O—CH$_2$—), 5.08-5.24 (m, 1H, O—CH—CH3); 5.78-5.87 (m, 1H, =C—H), 6.02-6.17 (m, 1H, =C—H); 6.34-6.44 (m, 1H, =C—H) ppm. $^1$H NMR spectra of acetoxypropyl acrylate is also illustrated in FIG. 1.

Note: Commercial HPA was a 2:1 mixture of the constitutional isomers 2-hydroxypropyl acrylate and 1-methyl-2-hydroxyethyl acrylate. Thus, the acetylated product was also a mixture, but the predominant isomer 2-propylacetyl acrylate is assumed for all further experiments.

Structural isomers of hydroxypropyl acrylate and acetoxypropyl acrylate.

Example 3: Synthesis of p(MA-Stat-CEA-Stat-HPA-Stat-PAA)

4-cyano-4-(propylsulfanylthiocarbonyl)sulfanylpentanoic acid (CPP) was synthesized according to literature procedure reported in Macromolecules 2008, 41, 8429-8435.

The copolymerization of methyl acrylate (MA), 2-carboxyethyl acrylate (CEA), 2-hydroxypropyl acrylate (HPA), and 2-acetoxypropyl acrylate (also 2-propylacetyl acetate acrylate, or PAA) was performed using RAFT polymerization with initiator AIBN and chain transfer agent CPP.

A dried 50 mL round bottom flask was charged with all monomers (MA, CEA, HPA, PAA), AIBN, and CPP in DMF solvent. The mixture was sealed and degassed under inert nitrogen at room temperature for about 25 min. An initial sample was taken to verify monomeric ratio feed, and the reaction vessel was submerged into a preheated, stirring oil bath maintained at 70° C. To monitor reaction progress, aliquots were taken periodically over time with a nitrogen-filled syringe via $^1$H NMR. Polymerizations were quenched after approximately three hours by cooling to 0° C. and opening the flask to air. The resultant polymer was precipitated into diethyl ether with minimum dichloromethane. This process was repeated three times to remove residual monomer and DMF. The precipitated sample was filtered, washed, and dried under vacuum. For all polymers, molecular weight and dispersity were verified with size exclusion chromatography (SEC), and chemical composition was calculated using quantitative proton nuclear magnetic resonance ($^1$H NMR) spectroscopy.

Figure 2:
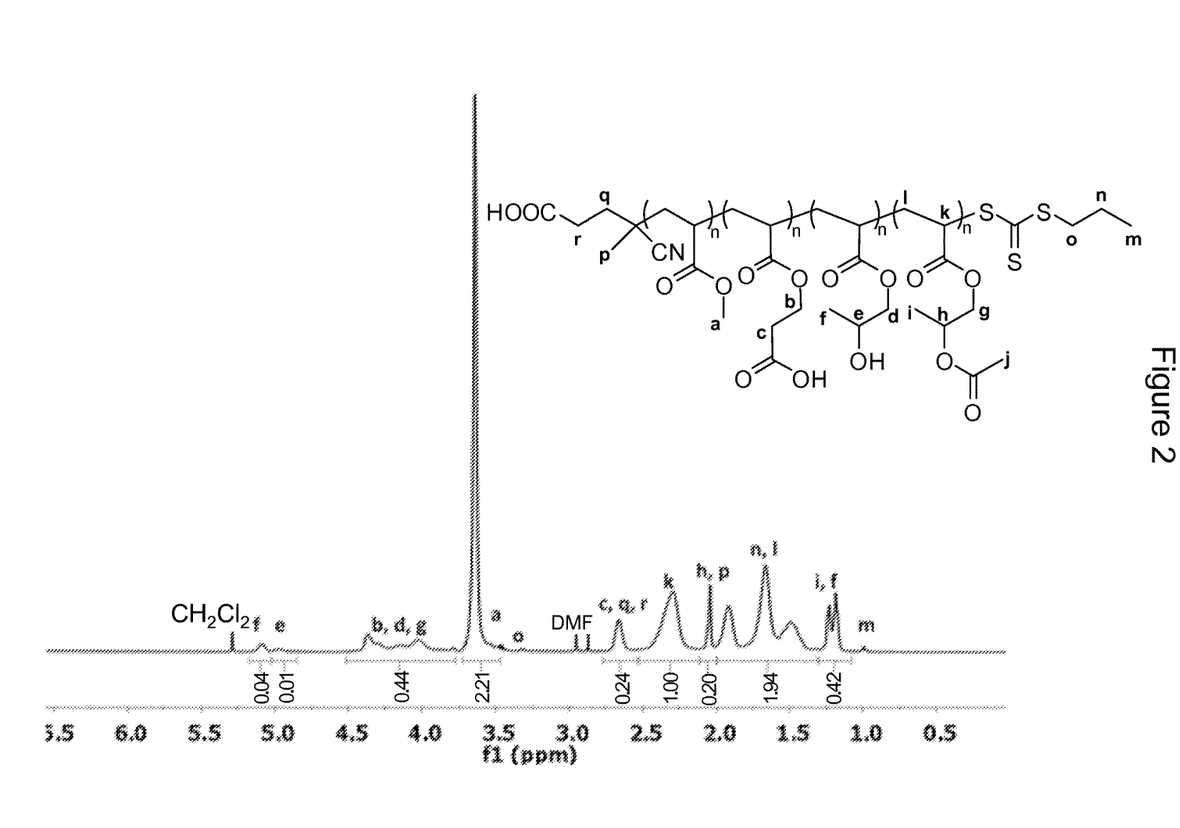
FIG. 2 shows $^1$H NMR spectra of p(MA-ran-CEA-ran-HPA-ran-PAA), where methyl acrylate is MA, 2-carboxyethyl acrylate is CEA, 2-hydroxypropyl acrylate is HPA, and 2-acetoxypropyl acrylate (also referred to as 2-propylacetyl acrylate) is PAA.

Polymer characterization was conducted using $^1$H NMR and SEC instruments. $^1$H NMR spectroscopy was carried out on a Varian Inova 500 spectrometer at 22° C. Representative $^1$H NMR spectra of p(MA-stat-CEA-stat-HPA-stat-PAA), which contains 77.4% MA (3.62 ppm, 3H), 7% CEA (2.63 ppm, 2H), 7.8% PAA (2.02 ppm, 3H), and 7.8% HPA (1.21 ppm, 3H), and which is represented in FIG. 2.

The percentage of each monomer in the polymer was calculated by comparing the characteristic monomer protons (OCH$_3$ for MA, —CH$_2$—COOH for CEA, C—CH$_3$ for HPA, and CH$_3$—CO for PAA) integrations with the polymer backbone protons at 1.90 ppm (1H, —CH—) and 1.3-2.0 ppm (2H, —CH$_2$—).

SEC measurements were conducted on an Agilent 1260 Infinity liquid chromatography system equipped with one Waters Styragel guard column and three Waters Styragel columns (HR6, HR4, and HR1) with pore sizes suitable for materials with effective molecular weights from 100 to 10,000,000 g/mol. The SEC is equipped with an Agilent 1260 Infinity Variable Wavelength Detector monitoring at 254 nm (80 Hz data collection frequency), a Wyatt Dawn Heleos II light scattering detector at a laser wavelength of 663.6 nm (18 angles from 10° to 160°), and a Wyatt Optilab T-rEX refractive index detector operating at 658 nm. THF was run as the mobile phase at 1.0 mL min$^{-1}$ at 25° C.

The following samples were made essentially according to the above described method, wherein the numbers correspond to the mole percent of each monomer.

TABLE 1

| Sample # | MA | CEA | HPA | PAA |
|---|---|---|---|---|
| 1 | 0.43 | 0.10 | 0.16 | 0.30 |
| 2 | 0.67 | 0.18 | 0.08 | 0.07 |
| 3 | 0.75 | 0.10 | 0.05 | 0.10 |
| 4 | 0.69 | 0.14 | 0.07 | 0.09 |

Example 4: The Dissolution of Probucol

The solubility of crystalline probucol in phosphate buffer was determined to be 4 µg/mL.

TABLE 2

Phenytoin dissolution control.

| Time (s) | Concentration (μg/mL) | Standard Deviation (μg/m) |
|---|---|---|
| 0 | 0 | 0 |
| 4 | 38 | 5 |
| 10 | 46 | 2 |
| 20 | 45 | 3 |
| 40 | 48 | 1 |
| 90 | 51 | 1 |
| 180 | 45 | 1 |
| 360 | 48 | 5 |

Example 5: Spray Drying Conditions

Spray dried dispersions were produced by spraying a 2 wt % solids solution in acetone in a Bend Research, Inc, mini-spray dryer at 12.8 slpm nitrogen flow rate, 80° C. inlet temperature, and 0.65 mL/min solution flow rate. Dispersions were collected on filter paper. Drug loading was calculated based on solids, e.g. 10% phenytoin loading in the final spray dried dispersion was produced from a solution of 1.8 wt % polymer and 0.2 wt % API in acetone.

TABLE 3

| Sample # | Spray-drying Ability | $T_g$ (° C.) |
|---|---|---|
| 1 | Poor | — |
| 2 | Poor | 20.0 |
| 3 | Poor | 10.6 |
| 4 | Poor | 20.3 |

Example 6: Dissolution Data

Probucol and phenytoin concentrations were quantified using a Agilent 1260 Infinity Quaternary HPLC equipped. The HPLC consisted of a reversed-phase EC-C18 column (Poroshell 120, 4.6×50 mm, 2.7 μm, Agilent, USA). The mobile phase was acetonitrile:water 96:4 for probucol and acetonitrile:water 40:60 for phenytoin, and the flow rate was 1.0 mL/min. A 10 μL aliquot of sample was injected, and the column effluent was detected at 241 nm for probucol (eluted at 2.90 min) and 225 nm for phenytoin (eluted at 1.40 min) with a UV detector (1260 Infinity Multiple Wavelength Detector, Agilent). The standard curve linearity was verified from 0.1 to 1000 μg/mL with an $r^2$ value of at least 0.999.

TABLE 4

Sample 2 with probucol dissolution performance.

| Time (s) | 10 wt % loading | | 25 wt % loading | | 50 wt % loading | |
|---|---|---|---|---|---|---|
| | Value | Uncertainty | Value | Uncertainty | Value | Uncertainty |
| 0 | 0 | 0 | 0 | 0 | 0 | 0 |
| 4 | 46 | 2 | 10 | 3 | 6 | 5 |
| 10 | 60 | 8 | 13 | 3 | 5 | 2 |
| 20 | 79 | 21 | 15 | 2 | 7 | 3 |
| 40 | 151 | 19 | 39 | 6 | 16 | 11 |
| 90 | 443 | 48 | 272 | 50 | 36 | 32 |
| 180 | 690 | 13 | 627 | 43 | 102 | 96 |
| 360 | 1047 | 147 | 1022 | 63 | 156 | 115 |

TABLE 5

Sample 3 with probucol dissolution performance.

| Time (s) | 10 wt % loading | | 25 wt % loading | | 50 wt % loading | |
|---|---|---|---|---|---|---|
| | Value | Uncertainty | Value | Uncertainty | Value | Uncertainty |
| 0 | 0 | 0 | 0 | 0 | 0 | 0 |
| 4 | 18 | 1 | 6 | 0 | 4 | 1 |
| 10 | 24 | 1 | 8 | 2 | 5 | 0 |
| 20 | 40 | 8 | 14 | 2 | 5 | 0 |
| 40 | 72 | 12 | 27 | 15 | 10 | 5 |
| 90 | 82 | 21 | 31 | 6 | 12 | 3 |
| 180 | 114 | 25 | 48 | 9 | 15 | 4 |
| 360 | 155 | 26 | 69 | 20 | 19 | 6 |

TABLE 6

Sample 4 with probucol dissolution performance.

| Time (s) | 10 wt % loading | | 25 wt % loading | | 50 wt % loading | |
|---|---|---|---|---|---|---|
| | Value | Uncertainty | Value | Uncertainty | Value | Uncertainty |
| 0 | 0 | 0 | 0 | 0 | 0 | 0 |
| 4 | 9 | 1 | 3 | 0 | 4 | 0 |
| 10 | 15 | 3 | 7 | 2 | 5 | 1 |
| 20 | 22 | 7 | 8 | 1 | 4 | 0 |
| 40 | 33 | 10 | 12 | 2 | 5 | 1 |
| 90 | 49 | 15 | 17 | 2 | 6 | 1 |
| 180 | 66 | 31 | 23 | 4 | 8 | 2 |
| 360 | 76 | 34 | 29 | 3 | 11 | 1 |

It is understood that the examples and embodiments described herein are for illustrative purposes only and that various modifications or changes in light thereof will be suggested to persons skilled in the art and are to be incorporated within the spirit and purview of this application and scope of the appended claims. All publications, patents, and patent applications cited herein are hereby incorporated herein by reference for all purposes.

What is claimed is:

1. A polymer having a backbone formed by reacting acrylate monomers with a free radical initiator in the presence of a chain transfer agent, wherein the polymer backbone consists of monomeric units derived from a monomer of formula I, a monomer of formula II, a monomer of formula III, and a monomer of formula IV, wherein formulae I-IV are:

(I)

(II)

-continued wherein
at each occurrence, $R_1$, $R_2$ and $R_3$ are independently H or methyl;
$R_4$ is H or $C_1$-$C_6$ alkyl;
$R_6$ is $C_1$-$C_6$ alkyl; and,
the monomer of formula I is present in the backbone at a mole percent of from about 40-80;
the monomer of formula II is present in the backbone at a mole percent of from about 5-20;
the monomer of formula III is present in the backbone at a mole percent of from about 5-20;
the monomer of formula IV is present in the backbone at a mole percent of from about 5-35.

2. A polymer according to claim 1, wherein at least one occurrence of $R_1$ is H.

3. A polymer according to claim 1, wherein at least one occurrence of $R_2$ is H.

4. A polymer according to claim 1, wherein at least one occurrence of $R_3$ is H.

5. A polymer according to claim 1, wherein $R_6$ is $C_1$-$C_4$ alkyl.

6. A polymer according to claim 1, wherein the monomer of formula (I) has the formula:

7. A polymer according to claim 1, wherein the monomer of formula (II) has the formula:

8. A polymer according to claim 1, wherein the monomer of formula (III) has the formula:

or combinations thereof.

9. A polymer according to claim 1, wherein the monomer of formula (IV) has the formula:

or combinations thereof.

10. A polymer according to claim 1, wherein the polymer is a statistical polymer.

11. A method of making the polymer of claim 1, comprising treating the at least three monomers, with a free radical initiator in the presence of a chain transfer agent.

12. A method according to claim 11, wherein the free radical initiator is AIBN.

13. A pharmaceutical formulation comprising the polymer of claim 1, and at least one active pharmaceutical ingredient.

14. A method of increasing the solubility of a drug, the method comprising formulating the drug with the polymer of claim 1.

15. A polymer according to claim 1, wherein the mole percent of monomers of formula I in the polymer backbone is from about 43 to about 75.

16. A polymer according to claim 1, wherein the mole percent of monomers of formula IV in the polymer backbone is from about 7 to about 30.

17. A polymer according to claim 1, wherein the mole percent of monomers of formula I in the polymer backbone is from about 43 to about 75, and the mole percent of monomers of formula IV in the polymer backbone is from about 7 to about 30.

* * * * *